United States Patent [19]

Fowler

[11] Patent Number: 5,070,094

[45] Date of Patent: Dec. 3, 1991

[54] N-BENZYLTROPANEAMIDES

[75] Inventor: Kerry W. Fowler, Seattle, Wash.

[73] Assignee: G. D. Searle & Co., Chicago, Ill.

[21] Appl. No.: 402,953

[22] Filed: Sep. 5, 1989

[51] Int. Cl.$^5$ .................... A61K 31/44; C07D 451/02
[52] U.S. Cl. .................................. 514/304; 546/124
[58] Field of Search .................... 546/124; 514/304

[56] References Cited

U.S. PATENT DOCUMENTS

| 3,907,810 | 9/1975 | Cavalla et al. | 546/210 |
|---|---|---|---|
| 3,910,931 | 10/1975 | Cavalla et al. | 546/206 |
| 3,910,932 | 10/1975 | Cavalla et al. | 546/194 |
| 3,912,741 | 10/1975 | Cavalla et al. | 546/202 |
| 3,917,614 | 11/1975 | Cavalla et al. | 546/208 |
| 3,919,242 | 11/1975 | Cavalla et al. | 546/197 |
| 4,028,365 | 6/1977 | Cavalla et al. | 546/200 |
| 4,029,801 | 6/1977 | Cavalla et al. | 514/329 |
| 4,045,444 | 8/1977 | Cavalla et al. | 546/194 |
| 4,046,767 | 9/1977 | Cavalla et al. | 546/197 |
| 4,061,640 | 12/1977 | Cavalla et al. | 546/175 |
| 4,138,492 | 2/1979 | Noverola et al. | 514/316 |
| 4,277,501 | 7/1981 | Melley et al. | 514/654 |
| 4,289,781 | 7/1981 | Bengtsson et al. | 514/323 |
| 4,596,827 | 6/1986 | Melley et al. | 514/605 |

FOREIGN PATENT DOCUMENTS 13138 7/1980 European Pat. Off. .
1345872 2/1974 United Kingdom .

OTHER PUBLICATIONS

Effects of a Unique, New, Antihypertensive Agent (MJ-14712) on Arterial Blood Pressure and the Blood Pressure Response to Tilt (Orthostatic Hypotensive Potential) in Conscious Rats and Dogs, Flemming, J. S., et al. *Federation Proceedings*, vol. 43, p. 553, 1984.
Chemical Abstracts Service CA 94:65477, Abstract of EP 13138.

*Primary Examiner*—Catherine S. Kilby Scalzo
*Attorney, Agent, or Firm*—Joy Ann Serauskas; Paul D. Matukaitis

[57] ABSTRACT

N-benzyl tropane amides, which have activity as Class III antiarrhythmic agents, acting by prolonging cardiac action potential repolarization. The invention further provides for compositions incorporating the compounds and methods of their use, as well as providing for pharmaceutically acceptable salts of the compounds.

13 Claims, No Drawings

N-BENZYLTROPANEAMIDES

BACKGROUND OF THE INVENTION

The present invention provides novel compounds, novel compositions, methods of their use and methods of their manufacture, such compounds pharmacologically useful in the treatment of cardiac arrhythmias. More specifically, the compounds of the present invention are class III antiarrhythmic agents which, by effectively prolonging repolarization of a cardiac cell action potential, can be used effectively to treat certain cardiac arrhythmias.

Antiarrhythmic drugs have been grouped together according to the pattern of electrophysiological effects that they produce and/or their presumed mechanisms of action. Thus, Class I antiarrhythmic agents are characterized by being sodium channel blockers, Class II antiarrhythmic agents are beta-adrenergic blockers, Class III antiarrhythmic agents prolong repolarization, and Class IV antiarrhythmic agents are calcium channel blockers.

Currently, there are very few Class III antiarrhythmic agents available for therapeutic use. Among them is bretylium. Bretylium's usefulness is limited, however, and currently its therapeutic use is reserved for life-threatening ventricular arrhythmias that are refractory to other therapy. Thus, bretylium's use is generally confined to intensive care units. It is an object of this invention to provide Class III antiarrhythmic agents of broader therapeutic use than existing Class III antiarrhythmic agents.

SUMMARY OF THE INVENTION

The invention relates to novel compounds of the general formula I:

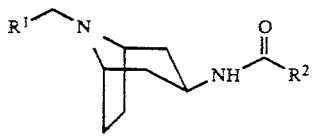

and the pharmaceutically acceptable salts thereof, wherein $R^1$ is unsubstituted aryl, substituted aryl, or alkyloxyaryl, in which alkyl is one to ten carbon atoms and wherein $R^2$ is cycloalkyl of three to eight carbon atoms, phenyl, phenyl substituted by alkyl of one to ten carbon atoms, fused polycycloalkyl, fused cycloalkylphenyl, fused cycloalkylphenyl wherein phenyl is substituted by alkyl of one to ten carbon atoms, or naphthalenyl or naphthalenyl substituted by alkyl of one to ten carbon atoms.

The compounds and pharmaceutical compositions thereof are useful in the antiarrhythmic methods of the invention. The invention further provides dosage unit forms adapted for oral, topical and parenteral administration. Also provided for in this invention are the pharmaceutically acceptable salts of the compounds.

DETAILED DESCRIPTION OF THE INVENTION

As used herein, the expression "aryl" is defined as phenyl. The term "substituted aryl" shall include phenyl substituted by alkyl of one to ten carbon atoms. The term "alkyloxyaryl" is defined to include alkyl of one to ten carbon atoms and aryl which may be unsubstituted phenyl or phenyl substituted by alkyl of one to ten carbon atoms. The term "alkyl" is defined to include straight or branched carbon-carbon linkages of one to ten carbon atoms. The term "fused polycycloalkyl" is defined to include two or more cycloalkyl rings fused together, each independently of three to eight carbon atoms. The term "fused cycloalkyl phenyl" is defined to mean phenyl fused to a cycloalkyl of five to eight carbon atoms.

The term "cardiac arrhythmia" is defined to mean any variation from the normal rhythm of the heartbeat, including, without limitation, sinus arrhythmia, premature heartbeat, heartblock, fibrillation, flutter, pulsus alternans, tachycardia, paroxysmal tachycardia and premature ventricular contractions.

The term "repolarization of cardiac cells" is defined as those phases of a cardiac action potential during which time a depolarized cardiac cell is reverting to normal pre-polarization transmembrane voltage.

The term "pharmaceutically acceptable salts" refers to non-toxic salts of the compounds of this invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, clavulanate and the like salts.

Compounds of the invention can be prepared readily according to the following reaction scheme or modifications thereof using readily available starting materials, reagents and conventional synthesis procedures. In these reactions, it is also possible to make use of variants which are in themselves known, but are not mentioned in greater detail.

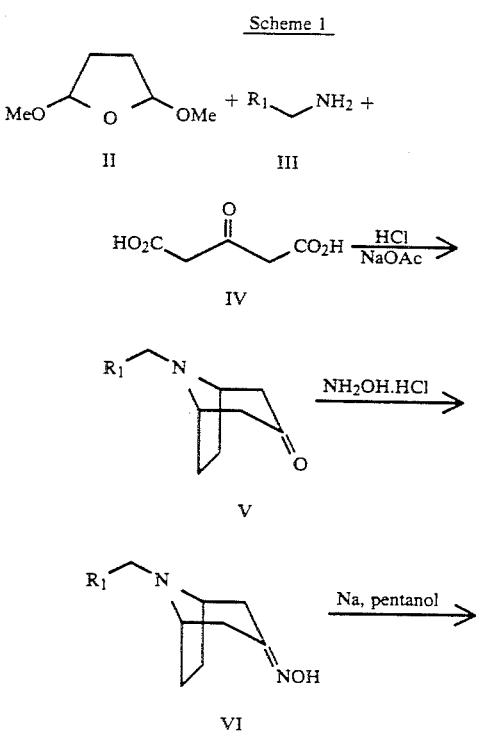

-continued
Scheme 1

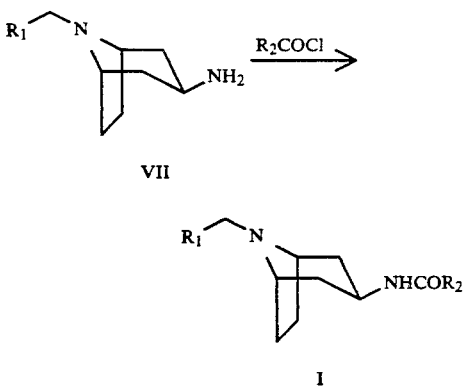

The compounds of the present invention can be administered in such oral dosage forms as tablets, capsules, pills, powders, granules, elixers, tinctures, suspensions, syrups and emulsions. Likewise, it can also be administered in intravenous, intraperitoneal, subcutaneous or intramuscular form, all using forms known to those of ordinary skill in the pharmaceutical arts. In general, the preferred form of administration is oral. An effective but non-toxic amount of the compound is employed in the treatment of arrhythmias of the heart. The dosage regimen utilizing the compound of the present invention is selected in accordance with a variety of factors including the type, species, age, weight, sex and medical condition of the patient; with the severity of the condition to be treated; the route of administration; the renal and hepatic function of the patient; and the particular compound employed or salt thereof. An ordinarily skilled veterinarian or physician can readily determine and prescribe the effective amount of the drug required to prevent, treat or arrest the progress of the condition.

Oral dosages of the compounds of the present invention, when used for the indicated cardiac effects, will range between about 0.1 mg per kilogram of body weight per day (mg/kg/day) to about 1000 mg/kg/day and preferably 1.0 to 100 mg/kg/day. Advantageously, the compounds of the present invention can be administered in a single daily dose or the total daily dosage can be administered in divided doses of two, three or four times daily.

In the pharmaceutical compositions and methods of the present invention, the compounds described in detail below will form the active ingredient that will typically be administered in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with conventional pharmaceutical practices.

For instance, for oral administration in the form of tablets or capsules, the active drug component can be combined with an oral non-toxic pharmaceutically acceptable inert carrier such as lactose, starch, sucrose, glucose, methylcellulose, magnesium stearate, dicalcium phosphate, calcium sulfate, mannitol, sorbitol and the like; for oral administration in liquid form, the active drug components can be combined with any oral non-toxic pharmaceutically acceptable inert carrier such as ethanol, glycerol, water, and the like. In the case of oral administration and in liquid form, suitable flavoring carriers can be added such as cherry syrup and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol and various waxes. Lubricants for use in these dosage forms include magnesium stearate, sodium benzoate, sodium acetate, sodium stearate, sodium chloride, sodium oleate and the like. Disintegrators include, without limitation, starch, methylcellulose, agar, bentonite, xanthan gum and the like.

The compounds of this invention can also be administered by intravenous route in doses ranging from 0.01 to 10 mg/kg/day.

Furthermore, it is also contemplated that the invention can be administered in an intranasal form topically via the use of suitable intranasal vehicles, or via transdermal routes, using those forms of transdermal skin patches well known to those of ordinary skill in that art. In the case of transdermal skin patch administration, daily dosage is continuous via the transdermal delivery system rather than divided, as in an oral delivery system.

The compounds of this invention exhibit antiarrhythmic activity useful in the treatment of various cardiac arrhythmias. The test procedures employed to measure this activity of the compounds of the present invention are described below.

EXAMPLE 1

Guinea pigs, of either sex weighing between 200–350 g, are acutely sacrificed and the right ventricular papillary muscle is isolated. A sample of a given test compound is added using an in vitro tissue bath. Concentrations used are generally $3 \times 10^{-5}$ M, but may also be as low as $3 \times 10^{-7}$ M. Changes in refractory period are measured before and after adding 1 concentration (usually $3 \times 10^{-5}$ M, as noted above) of a test compound to the bath. One hour is allowed for drug equilibration. A compound is considered active (Class III) if an increase in ventricular refractory period is 25 msec or more (at $3 \times 10^{-5}$ M).

| Compound | Results Concentration (M) | Change (msec) |
| --- | --- | --- |
| H$_2$O | — | 8 |
| Disopyramide | $3 \times 10^{-5}$ | 20 |
| Clofilium | $3 \times 15^{-5}$ | 24 |
| Sotalol | $3 \times 10^{-5}$ | 35 |
| Example 2 | $3 \times 10^{-5}$ | 75 |
| Example 3 | $3 \times 10^{-6}$ | 35 |

The following non-limiting examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Melting points were determined on a Thomas-Hoover Unimelt Capillary Apparatus and are not corrected. Unless otherwise noted, I.R. and NMR spectra were consistent with the assigned structure.

EXAMPLE 2

8-4[(4-methoxyphenyl)methyl]-8-azabicyclo[3.2.1]-octan-3-one oxime (VI, R$_1$=(4-methoxyphenyl)methyl).

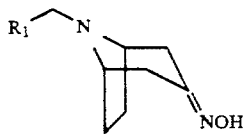

Following the general procedure previously described (P. Dostert, T. Imbert, M. Langlois, B. Bucher, and G. Mocquet, Eur. J. Med. Chem. Chim. Ther. 1984, 19, 105.), a mixture of 2,5-dimethoxy-tetrahydrofuran (8.22 g, 62.2 mmol) in 75 mL of 0.1 N HCl was heated at 80 °C. for 1 h then cooled to 10 °C. in an ice bath. Acetone 1,3-dicarboxylic acid (10.0 g, 68.4 mmol), 4-methoxybenzylamine (9.40 g, 68.5 mmol), 5.7 mL concentrated hydrochloric acid, and sodium acetate trihydrate (10.17 g, 74.7 mmol) were added and the reaction mixture was allowed to stir 18 h at room temperature. The solution containing the crude ketone V (R$_1$=(4-methoxyphenyl)methyl) was filtered through a pad of diatomaceous earth, treated with hydroxylamine hydrochloride (4.76 g, 68.5 mmol), stirred for 40 min, and brought to pH 8 with 50% aqueous NaOH solution. The gummy precipitate was partitioned between ethyl acetate and water, affording after removal of solvent 13.7 g of crude oxime VI (R$_1$=(4-methoxyphenyl) methyl) as a tan solid (85%). An analytical sample was recrystallized from acetonitrile to afford a white powder: mp 128°–131 °C. (corr). Anal. calcd. for C$_{15}$H$_{20}$N$_2$O$_2$: C, 69.21; H, 7.74; N, 10.76. Found: C, 69.16; H, 7.79; N, 10.93. $^1$H NMR δ (CDCl$_3$) 3.80 (s,3, OCH$_3$), 3.58 (s, 2, CH$_2$N).

EXAMPLE 3 exo-8-[(4-methoxyphenyl)methyl]-8-azabicyclo[3.2.1]octan-3-amine (VII, R$_1$=(4-methoxyphenyl)methyl).

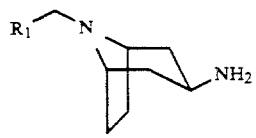

Following the general procedure previously described (P. Dostert, T. Imbert, M. Langlois, B. Bucher, and G. Mocquet, Eur. J. Med. Chem. Chim. Ther. 1984, 19, 105.), oxime VI (10.0 g, 38.4 mmol, R$_1$=(4-methoxyphenyl) methyl) was dissolved in 125 mL n-pentanol at 120 °C. in a 500 mL three-necked round-bottom flask equipped with a mechanical stirrer. The flask was removed from the heat and sodium metal (7.80 g, 0.339 g-atom) was added in small pieces at a rate sufficient to maintain the reaction temperature at 120°–130 °C. After the addition was complete the flask was heated to maintain this temperature until all the sodium had been consumed. The reaction mixture was cooled then poured onto 100 g of ice in a separatory funnel. After shaking the mixture, the pentanol layer was extracted thrice with 50 mL portions of 10% HCl. The combined acid washes were made basic with aq. NaOH and extracted thrice with 50 mL portions of ethyl acetate. The organic layer was washed with 50 mL water, 50 mL saturated brine, dried over sodium sulfate, and concentrated to afford the amine VII (R$_1$=(4-methoxyphenyl)methyl) as a clear light golden oil 8.73 g (92% crude) which was used without further purification: $^1$H NMR δ (CDCl$_3$) 3.78 (s, 3, OCH$_3$), 3.48 (s, 2, CH$_2$N), 2.93 (m, 1,-CHNH$_2$).

EXAMPLE 4

Preparation of exo-N-[8-[(4-methoxyphenyl)methyl)]-8-azabicyclo[3.2.1]oct-3-yl]benzamide

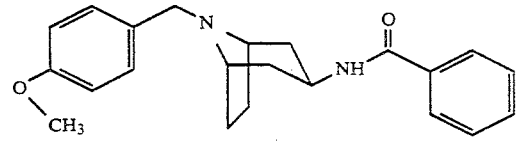

A solution of amine VII (0.975 g, 3.96 mmol) and triethylamine (0.7 mL, 5.0 mmol) in 10 mL CH$_2$Cl$_2$ was cooled in an ice bath and treated dropwise with benzoyl chloride (0.5 mL, 4.3 mmol). After 1 h the solution was washed with 10 mL 1 N NaOH, 10 mL water, dried over sodium sulfate, and concentrated to afford amide I (R$_1$=(4-methoxyphenyl)methyl, R$_2$=phenyl) as a solid.

Recrystallization from ethyl acetate gave the product as a white powder, 0.71 g (51%): mp 159.5°–161.0 °C. (corr). Anal. calcd. for C$_{22}$H$_{26}$N$_2$O$_2$: C, 75.40; H, 7.48; N, 7.99. Found: C, 75.37; H, 7.63; N, 7.97. $^1$H NMR δ (CDCl$_3$) 3.78 (s, 3, OCH$_3$), 3.47 (s, 2, CH$_2$N), 4.35 (cm, 1, CHNHCOPh).

EXAMPLE 5 exo-1,2,3,4-tetrahydro-N-[8-[(4-methoxyphenyl)-methyl)]-8-azabicyclo [3.2.1]oct-3-yl]-2-naphthalenecarboxamide

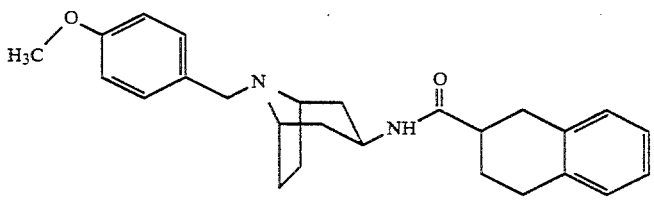

Following the procedure outlined in Example 4 and substituting 1,2,3,4-tetrahydro-2-naphthalenecarbonyl chloride as the acylating reagent, amine VII (1.30 g, 5.28 mmol, R$_1$=(4-methoxyphenyl)methyl) afforded I (1.33 g, 62%, R$_1$=(4-methoxyphenyl)methyl, R$_2$=phenyl) after recrystallization of the crude product from ethyl acetate: mp 189.5°–191.5 °C. (corr). Anal. calcd. for C$_{26}$H$_{32}$N$_2$O$_2$: C, 77.19; H, 7.97; N, 6.92. Found: C, 76.95; H, 8.02; N, 6.85. $^1$H NMR δ (CDCl$_3$) 3.79 (s, 3, OCH$_3$), 3.45 (s, 2, CH$_2$N), 4.18 (cm, 1, CHNHCOR$_2$)

While the invention has been described and illustrated with reference to certain preparative embodiments thereof, those skilled in the art will appreciate that various changes, modifications and substitutions can be made therein without departing from the spirit and scope of the invention. For example, effective dosages other than the preferred range as set forth herein above may be applicable as a consequence of variations in the responsiveness of the mammal being treated for severity of cardiac arrhythmia, dosage-related adverse effects, if any, and analogous considerations. Likewise, the specific pharmacological responses observed may vary according to and depending upon the particular active compounds selected or whether there are present certain pharmaceutical carriers, as well as the type of formulation and mode of administration employed, and such expected variations for differences in the results are contemplated in accordance with the objects and practices of the present invention. It is intended, therefore, that the invention be limited only by the scope of the claims which follow, and that such claims be interpreted as broadly as is reasonable.

What is claimed is:

1. A compound of the general formula

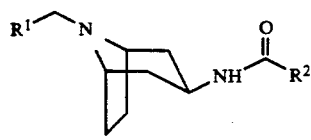

and the pharmaceutically acceptable salts thereof, wherein R¹ is unsubstituted or substituted aryl, or alkyloxyaryl, in which alkyl is one to ten carbon atoms and wherein R² is cycloalkyl of three to eight carbon atoms, phenyl, phenyl substituted by alkyl of one to ten carbon atoms, fused polycycloalkyl, fused cycloalkyl phenyl, fused cycloalkyl phenyl wherein phenyl is substituted by alkyl of one to ten carbon atoms, or naphthalenyl or naphthalenyl substituted by alkyl of one to ten carbon atoms.

2. A compound of the general formula

and the pharmaceutically acceptable salts thereof, wherein R¹ is methyloxyphenyl and R² is phenyl, cyclohexyl, tetralinyl, decalinyl or naphthalenyl.

3. A compound as claimed in claim 2, of the formula

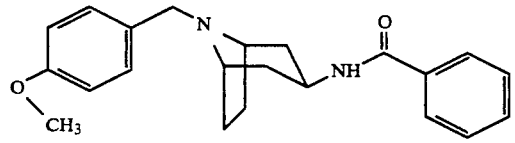

4. A compound as claimed in claim 2, of the formula

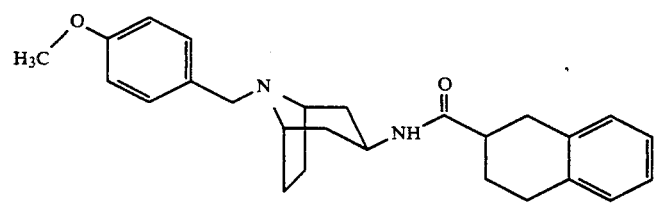

5. A pharmaceutical composition comprised of a pharmaceutically acceptable carrier in combination with a compound according to claim 1.

6. The composition as claimed in claim 5, wherein said compound is exo-N-[8-[(4-methoxyphenyl)methyl]-8-azabicyclo [3.2.1]oct-3-yl]benzamide.

7. The composition as claimed in claim 5, wherein said compound is exo-1,2,3,4-tetrahydro-N-[8-[(4-methoxyphenyl) methyl]-8-azabicyclo[3.2.1]oct-3-yl]-2-naphthalene carboxamide.

8. A method of regulating cardiac arrythmias in a mammal, comprising administering to said mammal a pharmacologically effective amount of a compound as claimed in claim 1.

9. A method as claimed in claim 8, wherein said compound is exo-N-[8-[(4-methoxyphenyl)methyl]-8-azabicyclo [3.2.1]oct-3-yl]benzamide.

10. A method as claimed in claim 8, wherein said compound is exo-1,2,3,4-tetrahydro-N-[8-[(4-methoxyphenyl) methyl]-8-azabicyclo[3.2.1]oct-3-yl]-2-naphthalenecarboxamide.

11. A method of prolonging repolarization of cardiac cells during a cardiac action potential in a mammal, comprising administering to said mammal a pharmacologically effective amount of a compound as claimed in claim 1.

12. A method as claimed in claim 11, wherein said compound is exo-N-[8-[(4-methoxyphenyl)methyl]-8-azabicyclo [3.2.1]oct-3-yl]benzamide.

13. A method as claimed in claim 11, wherein said compound is exo-1,2,3,4-tetrahydro-N-[8-[(4-methoxyphenyl) methyl]-8-azabicyclo[3.2.1]oct-3-yl]-2-naphthalenecarboxamide.

* * * * *